US00PP28714P3

(12) United States Plant Patent
Layt

(10) Patent No.: US PP28,714 P3
(45) Date of Patent: Nov. 28, 2017

(54) ***ANIGOZANTHOS* PLANT NAMED 'KP02'**

(50) Latin Name: ***Anigozanthos* hybrid**
Varietal Denomination: KP02

(71) Applicant: Todd Anthony Layt, Clarendon (AU)

(72) Inventor: Todd Anthony Layt, Clarendon (AU)

( * ) Notice: Subject to any disclaimer, the term of this patent is extended or adjusted under 35 U.S.C. 154(b) by 68 days.

(21) Appl. No.: 14/999,393

(22) Filed: May 2, 2016

(65) Prior Publication Data

US 2016/0330891 P1 Nov. 10, 2016

(30) Foreign Application Priority Data

May 6, 2015 (AU) ..... PBR 2015/096

(51) Int. Cl.
*A01H 5/02* (2006.01)

(52) U.S. Cl.
USPC ..... Plt./362

(58) Field of Classification Search
USPC ..... Plt./362
See application file for complete search history.

(56) References Cited

PUBLICATIONS

Domus Nursery—Catalogue List, http://www.domusnursery.com.au/dom_catalogue.jsp?Searched=Y&CategoryId=&Text=anigozanthos&GroupBy=ALPHA, downloaded Aug. 10, 2017.*

Google search using the date "Tool" prior to Apr. 22, 2015, C:\Users\agrunberg\Documents\e-RedFolder\14999393\anigozanthos kp02—Google Search.html.*

Wayback machine search on *Anigozanthos* 'KP02', https://web.archive.org/web/20140310035512/http://www.domusnursery.com.au/dom_stocklist.jsp?Searched=&CategoryId=&Text=&GroupBy=ALPHA), downloaded Aug. 18, 2017.*

* cited by examiner

*Primary Examiner* — Anne Grunberg
(74) *Attorney, Agent, or Firm* — Samuel R. McCoy, Jr.

(57) ABSTRACT

'KP02' is a distinctive cultivar of *Anigozanthos* hybrid plant which is characterized by the combination of a compact growth habit, narrow foliage, excellent disease resistance, and an abundance of golden yellow flowers. The new variety propagates successfully by division and tissue culture and has shown to be uniform and stable in the resulting generations from asexual propagation.

2 Drawing Sheets

Latin name of the genus and species: The Latin name of the genus and species of the novel variety disclosed herein is *Anigozanthos* hybrid.

Variety denomination: The inventive variety of *Anigozanthos* hybrid disclosed herein has been given the variety denomination 'KP02'.

BACKGROUND OF THE INVENTION

Parentage: 'KP02' is a seedling selection of unknown parentage which resulted from an open-pollination and seedling selection process carried out by the inventor at a commercial breeding facility in Clarendon, NSW, Australia. In 2010 and 2011, a number of *Anigozanthos* hybrid cultivars and a proprietary breeding line developed and owned by the same inventor, the seed parent, were grown in close proximity to one another in order to encourage open cross pollination. Cultivars included *Anigozanthos* hybrid 'Amber Velvet' (U.S. Plant Pat. No. 18,999), *Anigozanthos* hybrid 'Gold Velvet' (U.S. Plant Pat. No. 21,178), 'Regal Velvet' (not patented), and *Anigozanthos* hybrid 'Ruby Velvet' (not patented). In 2011, seeds were collected from the proprietary breeding line and germinated. The resulting seedlings were grown to maturity for further observation and, after the first flowering, a small number of plants were observed to exhibit a more compact growth habit and a greater number of inflorescences by comparison with the seed parent and each of the possible pollen parent cultivars. One progeny in particular was selected for commercialization in November of 2012 due to its narrow foliage, compact growth habit and an abundance of inflorescences bearing golden yellow flowers. This new and distinctive cultivar was given the name 'KP02'.

Asexual Reproduction: 'KP02' was first asexually propagated in November of 2012 by rhizome division in Clarendon, NSW, Australia and has since been asexually reproduced by meristematic tissue culture propagation. The distinctive characteristics of the inventive 'KP02' variety have proven to be stable through five generations and clones so produced maintain the distinguishing characteristics of the original plant.

SUMMARY OF THE INVENTION

The following traits have been repeatedly observed and represent the characteristics of the new cultivar. These characteristics, in combination, distinguish 'KP02' as a distinct cultivar of *Anigozanthos* hybrid:

1. 'KP02' exhibits narrow foliage; and
2. 'KP02' exhibits a compact growth habit; and
3. 'KP02' exhibits a very floriferous flowering habit; and
4. 'KP02' exhibits golden yellow flowers; and
5. 'KP02' exhibits high disease resistance.

BOTANICAL DESCRIPTION OF THE PLANT

Figure 1:
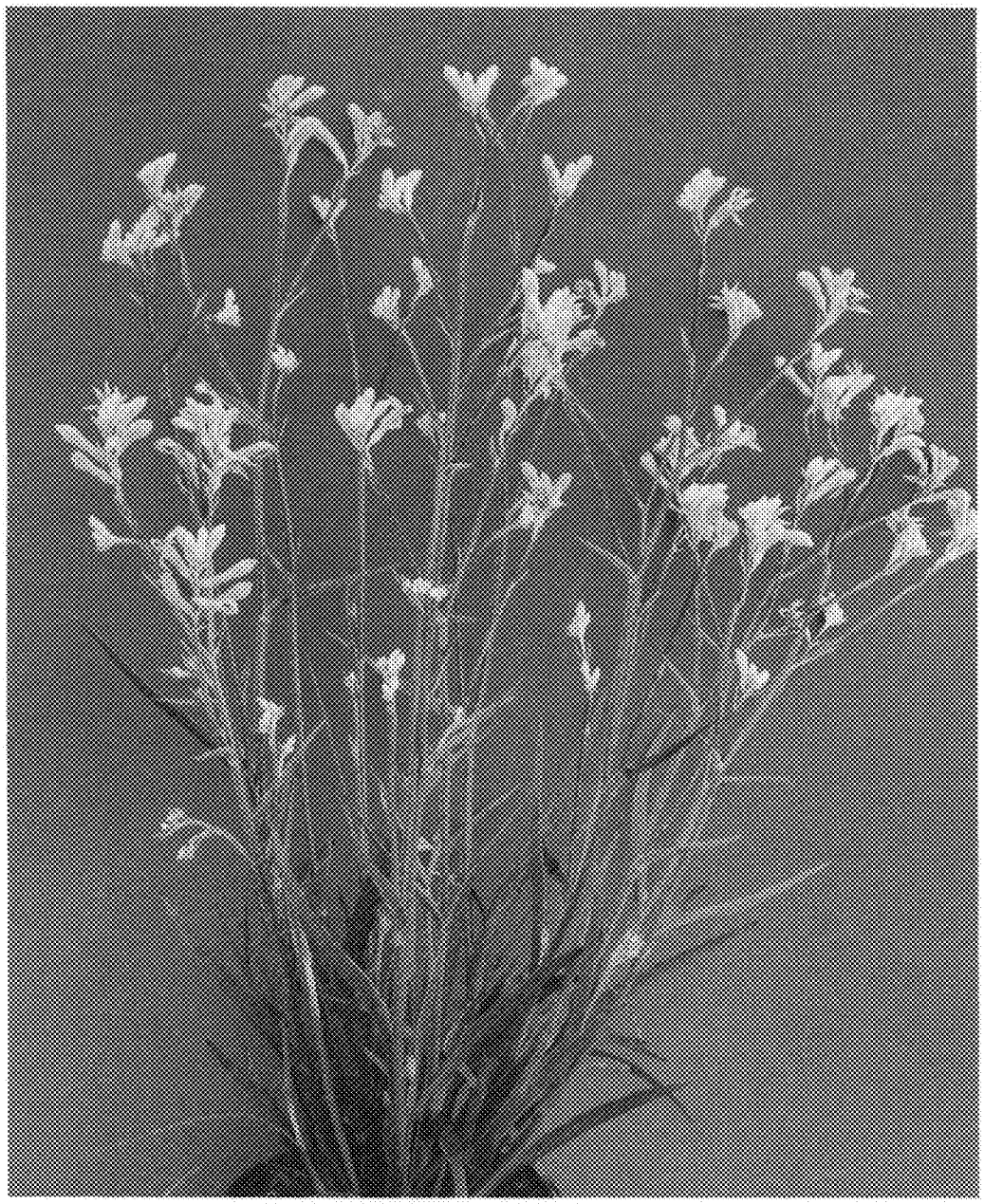
FIG. 1 illustrates, as true as is reasonably possible to obtain in color photographs of this type, an exemplary 'KP02' specimen. These 24 month old plants were grown outdoors in 300 mm nursery containers at a commercial plant breeding facility in Clarendon, NSW, Australia.
Figure 2:
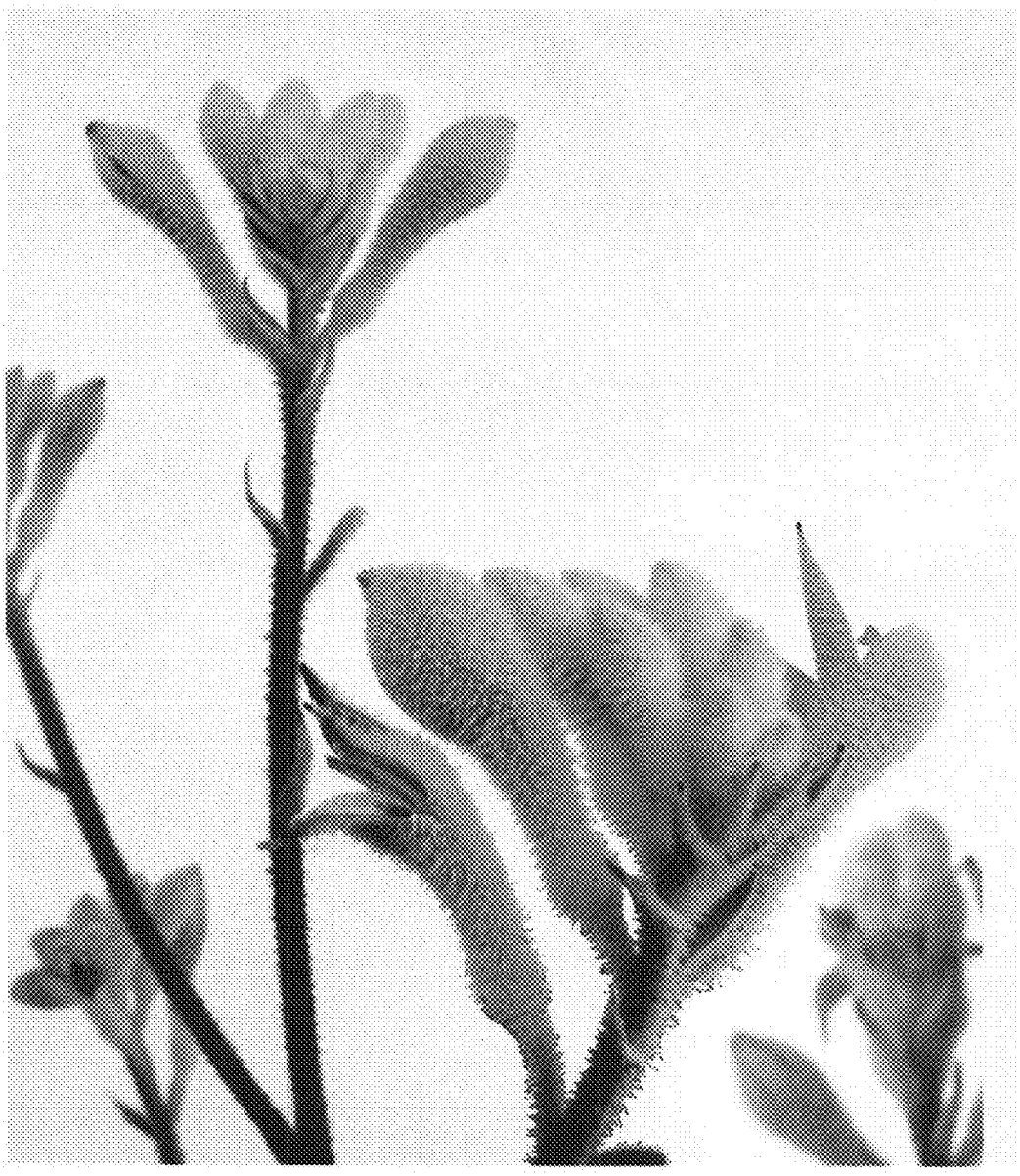
FIG. 2 illustrates, as true as is reasonably possible to obtain in color photographs of this type, an exemplary inflorescence of 'KP02', including buds and flowers.

The following is a detailed botanical description of a new and distinct variety of a *Anigozanthos* hybrid ornamental plant known as 'KP02'. Plant observations were made on plants grown in Clarendon, NSW, Australia. Unless indicated otherwise, the descriptions disclosed herein are based upon observations made in September 2015 of 36 month old 'KP02' plants. These plants were grown outdoors, in full sun, in 300 mm nursery pots filled with soilless potting media, maintained with granular slow release fertilizer and regularly watered with overhead irrigation. No pest and disease measures were taken.

Those skilled in the art will appreciate that certain characteristics will vary with older or, conversely, younger plants. 'KP02' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light intensity, day length, cultural conditions and the like. Color notations are based on *The Royal Horticultural Society Colour Chart*, The Royal Horticultural Society, London, 2001 Edition. Note that generic color descriptions such as 'green' do not exist in the R.H.S. charts and the corresponding R.H.S. colors are quoted.

A botanical description of 'KP02' and comparisons with the seed parent and several similar varieties of common knowledge are provided below.

General plant description:

*Plant habit*.—Strap-leaf herbaceous perennial with erect to semi-erect foliage; rhizomatous plant forming a clump.

*Height*.—40 cm.

*Width*.—40 cm.

*Hardiness*.—USDA Zone 9 to 11.

*Propagation*.—Propagation is accomplished by dividing the rhizomatous crown of the plant and also by way of meristematic tissue culture propagation.

*Crop time*.—Time to develop a rooted cutting is approximately 6 weeks, from division. An average crop time is approximately 4 to 6 months to produce a mature and marketable one gallon nursery container, beginning with a rooted cutting.

*Environmental tolerances*.—Tolerates full sun to partial shade, poor to fertile soils, and semi-regular watering or rainfall.

*Pest and disease susceptibility or resistance*.—No known pest or disease problems; excellent resistance to ink spot disease.

Roots: A network of thick, fleshy rhizomes with freely-branched fibrous roots.

Stems:

*Branching habit*.—Acaulescent, rhizomatous plant with shoots emerging upright at close to 90 degrees from the soil surface.

Foliage:

*Foliage abundance*.—Moderately abundant.

*Shape*.—Linear.

*Division*.—Simple.

*Arrangement*.—Equitant.

*Attachment*.—Radical.

*Apex*.—Subulate.

*Margins*.—Entire.

*Mature leaf dimensions*.—14 mm wide and 400 mm long, on average. The leaf thickness is 1.0 mm, on average.

*Juvenile foliage color, adaxial & abaxial surfaces*.—Yellow-green, RHS 146A.

*Mature foliage color, adaxial & abaxial surfaces*.—Yellow-green, RHS 146A.

*Venation*.—Parallel.

*Vein color, adaxial surfaces*.—Yellow-green, RHS 146A.

*Vein color, abaxial surfaces*.—Yellow-green, RHS 146A.

*Texture, adaxial surface*.—Smooth and glabrous.

*Texture, abaxial surface*.—Smooth and glabrous.

Inflorescence:

*Type*.—Compound one-sided raceme.

*Natural flowering season*.—August to October in NSW, Australia.

*Overall dimensions*.—Up to 750 mm long and 250 mm wide.

*Inflorescence attitude*.—Erect.

*Quantity*.—Medium to high; 10 inflorescence observed.

*Peduncle*.—Dimensions — Up to 750 mm long and 8 mm in diameter. Strength — Medium. Texture — Densely pubescent. Hairs are yellow-white, RHS 158D, on the lower portion and red, RHS 45A, on the upper portion. Color — Yellow-green, RHS 146A.

Bud:

*Dimensions*.—Approximately 28 mm long and 9 mm at the widest and 5 mm at the narrowest; 4.5 mm at the ovary.

*Bud shape*.—Tubular and globose at the distal end.

*Bud color*.—Yellow, RHS 9A, with slight intonations of red, RHS 45A, at the proximal end and yellow, RHS 12A, at the distal end.

Flower:

*Quantity*.—Approximately 40 flowers per inflorescence.

*Shape*.—Tubular.

*Persistence*.—Non-persistent.

*Lastingness*.—7 days.

*Aspect*.—Semi-erect.

*Fragrance*.—Non-fragrant.

*Pedicels*.—Dimensions — 5 mm long and 1.8 mm in diameter. Attitude — Semi-erect. Strength — Medium. Texture — Densely pubescent; hairs are red, RHS 45A. Color — Yellow-green, RHS 146A.

*Perianth*.—General description — Perianth is comprised of six tepals fused into a tube with tepal lobes at the distal end. Dimensions — Approximately 10 mm in diameter and 30 mm deep. Tepal lobe apex — Acute. Tepal lobe reflex — Strongly reflexed. Tepal lobe margin — Entire; not undulated. Texture and pubescence — Pubescent. Color when opening, inner surface — Yellow-green, RHS 144A. Color when opening, proximal end of outer surface —

Yellow, RHS 9A, with slight intonations of red, RHS 45A. Color when opening, distal end of outer surface — Yellow, RHS 12A. Color when fully opened, inner surface — Yellow-green, RHS 144A. Color when fully opened, proximal end of outer surface — Yellow, RHS 9A. Color when fully opened, distal end of outer surface — Yellow, RHS 12A.

*Floral bract*.—Quantity — One. Shape — Subulate. Apex — Apiculate. Base — Flat at fusion with the pedicel. Texture — Densely pubescent. Dimensions — Approximately 10 mm long and 5 mm wide at the base. Color, inner surface — Yellow-Green, RHS 144A. Color, outer surface — Yellow, RHS 9A, with slight intonations of greyed-red 178A.

Reproduction organs:

*Stamens*.—Quantity — Six adnate stamens. Filament — Approximately 30 mm long and 0.25 in diameter; color is yellow, RHS 7D. Anther — Two-lobed; oblong to linear; basifixed; approximately 3 mm long and 0.8 mm in diameter; color is yellow, RHS 14B. Pollen — Low amount of pollen present; color is closest to yellow, RHS 11C.

*Pistil*.—Quantity — One. Dimensions — Approximately 30 mm long and 0.5 in diameter. Stigma — Linear; approximately 29 mm long; color is green-white, near 157A. Style — Curved; 1 mm tall and 1 mm in diameter; color is yellow, RHS 14B. Ovary — Position is superior; 4 mm tall and 4 mm in diameter; color is yellow, RHS 9A.

Fruit and seed:

*Fruit*.—Ovoid capsules are 8 mm long and 6 mm in diameter; color is yellow, RHS 9A, and fade to brown, RHS 200.

*Seed*.—Irregular, angular; approximately 1 mm in diameter; color is dark grey to black, nearest to RHS 202A.

Comparisons With the Parent Plant

Plants of the new cultivar 'KP02' may be distinguished from the seed parent, a proprietary *Anigozanthos* hybrid breeding line, by the quantity of flowers produced. 'KP02' exhibits a high flower count, whereas the seed parent exhibits a low flower count.

Comparisons With the Most Similar Variety of Common Knowledge

Plants of the new cultivar 'KP02' may be distinguished from the commercial variety, *Anigozanthos* hybrid 'Gold Velvet', by the following combination of characteristics:

1. 'KP02' exhibits a long perianth tube, whereas 'Gold Velvet' exhibits a short perianth tube.
2. 'KP02' exhibits narrow leaves that are approximately 14 mm wide, whereas 'Gold Velvet' exhibits leaves of medium width, approximately 20 mm wide.

That which is claimed is:

1. A new and distinct variety of *Anigozanthos* hybrid plant named 'KP02', substantially as described and illustrated herein.

* * * * *